(12) United States Patent
Sein et al.

(10) Patent No.: US 8,952,063 B2
(45) Date of Patent: Feb. 10, 2015

(54) SATIETY-INDUCING COMPOSITION

(71) Applicant: DSM IP Assets B.V., Heerlen (NL)

(72) Inventors: Arjen Sein, Leiden (NL); Damiet Josephina Petronella Cunera Koenders, Den Haag (NL); Annika Viberg, Järfälla (CH); Gerardus Johannes Franciscus Smolders, Delft (NL); Anthonius Cornelis Van Den Vurg, Rijswijk (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/890,808

(22) Filed: May 9, 2013

(65) Prior Publication Data
US 2013/0253058 A1 Sep. 26, 2013

Related U.S. Application Data

(62) Division of application No. 13/262,672, filed as application No. PCT/EP2010/051574 on Feb. 9, 2010, now Pat. No. 8,530,514.

(30) Foreign Application Priority Data

Apr. 3, 2009 (EP) .................................. 09157263

(51) Int. Cl.
| | | |
|---|---|---|
| *A61K 31/20* | (2006.01) | |
| *A61K 31/19* | (2006.01) | |
| *A23C 9/13* | (2006.01) | |
| *A23L 1/29* | (2006.01) | |
| *A23L 1/30* | (2006.01) | |
| *A23L 1/307* | (2006.01) | |
| *A61K 31/23* | (2006.01) | |

(52) U.S. Cl.
CPC .............. *A61K 31/20* (2013.01); *A23C 9/1315* (2013.01); *A23L 1/293* (2013.01); *A23L 1/3006* (2013.01); *A23L 1/307* (2013.01); *A61K 31/23* (2013.01); *A23L 1/3008* (2013.01)
USPC ............................ 514/558; 514/553; 514/557

(58) Field of Classification Search
CPC ........ A61K 31/20; A61K 31/23; A61L 1/293; A61L 1/3006; A61L 1/3008; A61L 1/307
USPC ......................................... 514/553, 557, 558
See application file for complete search history.

(56) References Cited

U.S. PATENT DOCUMENTS

| | | | | |
|---|---|---|---|---|
| 3,492,130 A | * | 1/1970 | Harwood ....................... | 426/607 |
| 5,424,091 A | * | 6/1995 | Cain et al. ..................... | 426/610 |
| 5,514,406 A | | 5/1996 | Aoe et al. | |
| 5,871,799 A | | 2/1999 | Aoe et al. | |
| 8,426,469 B2 | * | 4/2013 | Horvath ........................ | 514/560 |
| 8,530,514 B2 | * | 9/2013 | Sein et al. ..................... | 514/558 |
| 2006/0105093 A1 | | 5/2006 | Bialek et al. | |
| 2009/0281185 A1 | | 11/2009 | Horvath | |

FOREIGN PATENT DOCUMENTS

| | | |
|---|---|---|
| CN | 1268869 | 4/2000 |
| JP | 63-501425 | 6/1988 |
| JP | 7-507546 | 8/1995 |
| WO | 87/03198 | 6/1987 |
| WO | 93/24113 | 12/1993 |
| WO | WO 99/02041 | 1/1999 |
| WO | WO 99/57990 | 11/1999 |
| WO | WO 01/76331 | 10/2001 |
| WO | WO 02/00042 A2 | 1/2002 |
| WO | WO 2005/074720 | 8/2005 |

OTHER PUBLICATIONS

International Search Report for PCT/EP2010/051574, mailed Apr. 19, 2010.
Written Opinion for PCT/EP2010/051574, mailed Apr. 19, 2010.
"Palm Öl", In: S.W.Souci et al., "Die Zusammensetzung der Lebensmittel Nahrwert", *MedPharm Scientific Publishers*, 2008, p. 207.
H. Woidich et al., "Uber die Zusammensetzung der Kakaobutter", vol. 125, No. 2, Aug. 1964, pp. 91-96.
Diepvens et al., "Long-term effects of consumption of a novel fat emulsion in relation to body-weight management", *International Journal of Obesity*, vol. 31, No. 6, Jun. 2007, pp. 942-949.
Diepvens et al., "Short-term effects of a novel fat emulsion on appetite and food intake", *Physiology & Behavior*, vol. 95, No. 1-2, Sep. 2008, pp. 114-117.
Dobson et al., "Does the site of intestinal delivery of oleic acid alter the ileal brake response", *International Journal of Pharmaceutics*, vol. 195, No. 1-2, Feb. 2000, pp. 63-70.
French et al., "The effects of intestinal infusion of long-chain fatty acids on food intake in humans", *Gastoentology*, vol. 119, No. 4, Oct. 2000, pp. 943-948.
Haenni et al, "Effect of fat emulsion (Fabuless) on orocecal transit time in healthy men," Scandinavian Journal of Gastroenterology, 2009, 44: pp. 1186-1190, XP008120748.
Blanch, et al, "Utilization of different fats and oils by adult chickens as a source of energy, lipid and fatty acids," Animal Feed Science Technology 61, 1996, pp. 335-342, Spain.

* cited by examiner

*Primary Examiner* — My-Chau T Tran
(74) *Attorney, Agent, or Firm* — Nixon & Vanderhye P.C.

(57) ABSTRACT

The present invention relates to the field of weight management. The invention particularly relates to a method for inducing satiety. In one of its embodiments, the present invention provides a method for inducing satiety in a human or an animal comprising administering to said human or animal an effective amount of a composition comprising a lipid of which at least part is in a crystal form in the small intestine.

20 Claims, No Drawings

SATIETY-INDUCING COMPOSITION

CROSS-REFERENCE

This application is a divisional of commonly owned copending U.S. application Ser. No. 13/262,672, filed Dec. 20, 2011 (now U.S. Pat. No. 8,530,514), which is the national phase application of International Application PCT/EP2010/051574, filed Feb. 9, 2010, which designated the US and claims benefit of EP Patent Application No. 09157263.6, filed Apr. 3, 2009, the entire contents of each of which are hereby incorporated by reference.

FIELD OF THE INVENTION

The present invention relates to the field of weight management. The invention particularly relates to a method for inducing satiety.

BACKGROUND OF THE INVENTION

The World Health Organization (WHO) has declared overweight as one of the top ten risk conditions in the world and one of the top five in developed nations (WHO). In most populations, the prevalence of overweight and obesity has steadily increased over the past 20 years (Vasan, R S et al., 2005). As such, increasing relative weight trends in populations have caused much concern among health care providers (Hill J O et al., 2003). Given the growing prevalence of overweight and related health consequences, there is a critical need for affordable and effective weight management strategies.

As a non-invasive primary treatment strategy for overweight and obesity, reduced-energy diets (appetite suppression) are a widely-recommended approach. Using data from national surveys, it was estimated that affecting energy balance by 100 kilocalories per day (e.g. ~4% of daily energy intake), weight gain in most of the US population could be prevented (Hill et al, 2003). It is in this context that ingredients that are designed to affect mechanisms regulating satiety may play a role, especially if these could be incorporated into every day foods.

Gastrointestinal signals are crucial for the regulation of food intake, satiety and satiation. Satiety feelings on a meal-to-meal basis are to a large extent determined by a coordinated series of neural and humoral signals that originate from the gut in response to mechanical and chemical properties of ingested food (Woods S C et al., 2004).

An option to prolong satiety and to reduce food intake is by delaying gastric emptying and/or small intestinal transit time (Geliebter A et al., 1988) (Jones K L et al., 1997) (Hveem K et al., 1996). This may be achieved by activation of the ileal brake (Van Citters G W et al., 1999). The ileal brake is the primary inhibitory distal-to-proximal feedback mechanism that controls meal transit through the gastrointestinal tract and is thought to regulate and optimize nutrient digestion and absorption (Van Citters G W et al., 1999).

It has been demonstrated that postprandial infusion of a small amount of fat into the ileum reduces hunger and increases satiety. Presence of fat in small intestine is associated with modulation of gastric emptying (Heddle R et al., 1989), and gastrointestinal hormone secretion (Macintosh C G et al., 1999), including CCK from the proximal (Buffa R et al., 1976), and peptide YY (PYY) from the distal (Adrian T E, et al., 1985), small intestine. Fat in the (distal part of the) small intestine also has the capacity to suppress appetite and energy intake (Chapman I M et al., 1999).

Several studies have shown that direct delivery of lipids into the ileum delays gastric emptying, (Welch I M et al., 1988), prolongs small intestinal transit time (Read N W et al., 1984) and induces satiety (Welch I et al., 1985).

Long-chain fatty acids are potent triggers of the ileal brake, (Van Citters G W et al., 1999) (Read N W et al., 1984), and several studies have demonstrated that the ileal brake is already activated by small amounts of fat or free fatty acids (Keller J et al., 2006) (Pironi L et al, 1993) (Dobson C L et al., 1999). The effects of free fatty acids on gastrointestinal function, including motility, hormone release, and energy intake (Feltrin K L et al., 2004) (Hunt J N et al., 1968) (Matzinger D et al., 2000) (McLaughlin J et al., 1999), also are dependent on their acyl chain length. Hunt and Knox (Hunt J N et al., 1968) were the first to demonstrate that fatty acids with a chain length of 12 and more carbon atoms empty from the stomach much slower than fatty acids containing 10 or fewer carbon atoms.

The mechanisms by which long fatty acid chain (>C12) inhibits subsequent energy intake are unclear. There is some evidence that the effects of long chain fatty acids are dependent on the release of CCK (Lal S et al., 2004); for example, the inhibitory effects of C12 on gastric emptying and the perception of intragastric volume are attenuated by the CCK1 receptor antagonist loxiglumide (Lal S et al., 2004). The effects of fatty acids also appear to involve the activation of vagal afferents, either directly or via CCK (Cox J E et al., 2004) (Lal S et al., 2001). The effects of C12 on energy intake may also be mediated through the actions of GLP-1 (Feltrin K L et al., 2004), and possibly other peptides, and by the changes in gastrointestinal motility, perhaps particularly the stimulation of pyloric motility (Xu X et al., 2005).

Fat Metabolism

Most dietary lipids are absorbed in the proximal two thirds of the jejunum. Normally, more than 94 percent of dietary fat is absorbed. Dietary lipids, consisting mostly of triglycerides, must be emulsified to expose a large surface area to lipolytic enzymes. Emulsification begins in the upper gastrointestinal tract through mastication and gastric mixing. Fat droplets released by these mechanical means are coated with phospholipids to form a stable emulsion. Ingested phospholipids (mostly phosphatidylcholine) exist in a ratio to triglycerides of approximately 1:30, which is adequate for coating. Additional phospholipid from bile is added once the emulsion reaches the duodenum.

Fat hydrolysis begins in the stomach by the actions of lingual lipase, and gastric lipase. Free fatty acids released by gastric lipolysis contribute to the stimulation of pancreatic lipase and colipase, which are responsible for the majority of lipid hydrolysis.

The lipid emulsion in the duodenum is then exposed to pancreatic lipase and degraded to monoglycerides and fatty acids. In this form the lipids are solubilised into small lipid particles also known as mixed micelles, consisting of phospholipids and bile. These mixed micelles transport the free fatty acids and monoglycerides to the intestinal wall, where the lipids are absorbed over the intestinal wall.

Despite great progress in the identification of central signals that regulates satiety, and considerable investment in the development of appetite-controlling medications, improvements are required.

SUMMARY OF THE INVENTION

The inventors have identified a novel way in which satiety can be induced. It is shown that upon administering certain lipids part of said lipids adopt—optionally after gastro-intestinal lipolysis—a crystal form in the gastro-intestinal tract. Without being bound by theory it is thought that these crystal lipids are not or only poorly absorbed in the jejunum and are transported to the lower, more distal parts of the small intestine. It is thought that the rate of absorption of the lipids by the body is reduced if the lipids are in a crystal form. In the lower part of the small intestine (i.e. the ileum) the crystals slowly redissolve into mixed micelles through which the lipids can be transported to the ileal wall and be absorbed by the body. It is thought that As a consequence, the body notices that lipids are still present in the more distal parts of the small intestine. The body then signals to the brain that it is in a satiated state and signals to the stomach to reduce gastric emptying: the ileal brake mechanism. In other words, modulation of the lipid absorption in the gastro-intestinal tract is used to trigger satiety. The invention thus also relates to the use of fatty acid crystals, in particular in the gastro-intestinal tract, and more particular in the ileum, to increase satiety in a human or animal.

DETAILED DESCRIPTION OF THE INVENTION

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. Crystal and crystalline are used interchangeably herein.

% of lipids described are in weight percentages based on the weight of the total amount of lipids (i.e. w/w %) unless stated otherwise.

The articles "a" and "an" are used herein to refer to one or to more than one (i.e. to one or at least one) of the grammatical object of the article. By way of example, "an element" may mean one element or more than one element.

In one of its embodiments, the present invention provides a method for inducing satiety in a human or animal comprising administering to said human or animal an effective amount of a composition comprising a lipid of which at least part is in a crystal form in the small intestine.

Preferably such a method is a cosmetic or non-therapeutic method. The invention also provides a method of treating a subject (i.e. animal or human) for therapeutic purposes which will be discussed in more detail later on.

Hence, the invention provides a method which can be used for a therapeutic, reason (for example in an individual who is classified as overweight), for a prophylactic reason or for a cosmetic or other non-therapeutic reason (for example in an individual who is not classified as being overweight).

The invention provides a method for inducing satiety, i.e. a method for inducing postprandial events that reduce the need for eating and affect the interval to the next meal and thereby regulating meal frequency or meal size, as well as reducing eating or snacking in between meals. This may also be referred to as a method for providing an appetite suppressing effect.

Alternatively, the invention provides a method for providing lipid crystal formation in the gastro-intestinal track, in particular in the small intestine of a human or animal comprising administering to said human or animal an effective amount of a lipid. Additionally the invention provides a method for providing lipid crystals in the gastro-intestinal track, in particular in the small intestine of a human or animal, comprising administering to said human or animal an effective amount of lipid crystals. A method according to the invention can be used to induce satiety in a subject such as a human or a (non-human) animal. Preferably, a method according to the invention is used to induce satiety in a human.

The lipid used to induce satiety is provided enteric or preferably orally. As will be discussed in more detail later on, part of the provided lipid is able to adopt a crystal structure during its passage through the gastro-intestinal tract or at least part of the lipid has been treated such that at least part of said lipid has a crystal structure before administering. Moreover, said lipid can also be formed as a result of lipolysis and subsequently adopt a crystal structure. Independent of the route chosen, part of said lipid is in a crystal structure. A crystal (or crystalline solid) is a solid material whose constituent atoms, molecules or ions are arranged in an orderly repeating pattern extending in all three spatial dimensions. A crystal can have different shapes or structures. In a preferred embodiment, part of the lipid used in a method according to the invention is capable of adopting a needle-like structure or shape. The average length of such a needle can be between 5 and 50 µm, with an average size of approximately 20 µm as observed by light microscopy. Typically the mentioned crystal size refers to single crystals, aggregates of multiple single, separate crystals can be larger. The crystals can be needle-shaped and as such can have a typical aspect ratio (length over width) of at least 5.

As disclosed within the experimental part herein, crystals were seen in jejunal samples from people who consumed a certain lipid. In one of its aspects the used lipid must be able to adopt a crystal structure in the small intestine, more preferably in the jejunum or before the lipids enter the jejunum. The invention thus provides a method for inducing satiety in a human or animal comprising administering to said human or animal an effective amount of a composition comprising a lipid of which at least part is in a crystal form in the small intestine, wherein at least part of said lipid is in a crystal form in the jejunum.

Comparable crystal structures can also be present in, for example, the stomach, duodenum and/or in the ileum (i.e. the distal, lower, part of the small intestine).

When analysing such a sample drawn from a human being or non human animal at least 20% (w/w) of the lipids in such a sample is typically in a crystal form, determined on differences seen in lipid compositions of formulations that do form crystals and other formulations that do not or hardly not form such crystals (such as for example a sample drawn for a human or animal body which was allowed to ingest milk comprising dairy fat).

The term "a lipid of which at least part is in a crystal form" as used herein therefore typically refers to "a lipid of which at least 20% by weight based in on the total weight of the lipid is in a crystal form (in the small intestine, preferably the jejunum). More preferably, this refers to at least 25 w/w %, 30 w/w %, 35 w/w %, 40 w/w %, 45 w/w %, 50 w/w % or even higher such as at least 60 w/w %, 70 w/w %, 80 w/w %, 90 w/w %.

The used lipid is typically part of a solid or liquid composition. Other components of such a composition can be an emulsifier (as will be discussed in more detail later on) or a flavour component or a preservative. Preferably said composition comprises a lipid as well as an emulsifier. In another aspect, the lipid is the sole (active, i.e. satiety inducing) ingredient of the composition, preferably in a dispersion wherein the lipid is dispersed in small particles (of less than 100 µm) in an aqueous phase. Preferably, said aqueous phase comprises for example at least one additional component selected from a protein, a carbohydrate, a flavor, a preservative, an artificial sweetener or a fibre. In yet another aspect the lipid (possibly with emulsifier) is the sole (active, i.e. satiety inducing) ingredient of the composition, preferably in a dispersion wherein the lipid is present in small particles (of less than 100 µm) within a solid carrier. Preferably, said solid carrier comprises for example maltodextrine or glucose syrup and may contain also at least one additional component selected from a protein, a carbohydrate, a flavor, a preservative, an artificial sweetener or a fibre.

The type of lipid can be diverse and is for example a triglyceride, a diglyceride, a monoglyceride or a free fatty acid or a salt of a free fatty acid. The invention thus provides a method for inducing satiety in a human or animal comprising administering to said human or animal an effective amount of a composition comprising a lipid of which at least part is in a crystal form in the small intestine, wherein said lipid comprises, preferably, is a triglyceride, a diglyceride, a monoglyceride or a free fatty acid or a salt of a free fatty acid. Preferably said lipid is a monoglyceride or a free fatty acid or a salt of a free fatty acid or a combination thereof. More preferably said lipid is a free fatty acid or a salt of a free fatty acid. Moreover, the term 'lipids' is used to refer to lipidic components resulting from lipolysis. The term 'lipids' therefore includes lipidic components resulting from lipolysis in the gastro-intestinal tract.

The term "triglyceride" as used herein refers to triacylglycerol (or triacylglyceride), that is glycerol esterified to three fatty acid chains.

The term "diglyceride" or diacylglycerol is used to refer to a glyceride consisting of two fatty acid chains covalently bonded to a glycerol molecule through ester linkage. A diglyceride can be a 1,2-diglyceride or a 1,3-diglyceride.

The term "monoglyceride" (or alternatively a monoacylglycerol) is typically used to describe a glyceride consisting of one fatty acid chain covalently bonded to a glycerol molecule through an ester linkage. A monoglyceride can be a 1-monoglyceride or a 2-monoglyceride.

The term "fatty acid" is used to refer to aliphatic monocarboxylic acid, derived from, or contained in esterified form in an animal or vegetable fat, oil or wax. Natural fatty acids commonly have a chain of four to 28 carbons (usually unbranched and even numbered), which may be saturated or unsaturated (cis or trans, mono or polyunsaturated). The term "free fatty acid" is used to refer to a non glycerol-esterified aliphatic monocarboxylic acid.

The term "salt of a free fatty acid" is used to refer to a free fatty acid which has formed a linkage with a salt, such as but not limited to, sodium (Na), potassium (K) or calcium (Ca).

A commercial source for any of these lipids can be either animal or vegetable and they may be synthetically made as well. The term synthetic or semi-synthetic refers to substances that are not entirely natural and/or obtained by chemical synthesis.

The triglyceride oils are preferably confectionery fats, such as palm oil, shea butter, allanblackia oil, cocoa butter or other. Other examples of such oils are fully hydrogenated or partly hydrogenated soybean oil, rapeseed oil, corn oil, cotton oil and sunflower oil and the like, or fractions thereof. Alternatively the triglyceride composition can be obtained through interesterification of blends of aforementioned oils.

The invention, amongst others, refers to a method wherein the triglyceride oils comprise a fraction of an oil or a fat, such as a fraction of palm oil. That is to say, a triglyceride oil used in the invention may be obtained from fractionated palm oil. This fraction of palm oil may be obtained from commercial palm oil, which may be fractionated to specific mixtures of suitable triglycerides, based on the combination of mainly palmitic, oleic, linoleic and stearic esters of glycerol, respectively, or from (partially) hydrogenated and optionally interesterified oils from other origin as described above. Fractions of palm oil are known as for instance palm stearine.

Preferred fatty acids for use in the invention are therefore selected from the group consisting of palmitic acid, oleic acid, linoleic acid and stearic acid. Even more preferred compositions comprise at least two fatty acids selected from the group consisting of palmitic acid, oleic acid, linoleic acid and stearic acid.

Particularly good results were achieved when 20-95 w/w %, such as 20-80 w/w % or such as 30-70 w/w % of fatty acids were used selected from the group consisting of palmitic and stearic acid, and 5-95 w/w %, such as 80-20 w/w % or such as 70-30 w/w % fatty acids selected from the group consisting of oleic and linoleic acid. It should be noted that these amounts do not necessarily have to add up to 100 w/w %, i.e. they do not necessarily exclude the presence of additional fatty acids such as lauric acid, myristic acid and linolenic acid.

In another aspect of the invention at least 80 w/w %, preferably at least 90 w/w % of the fatty acids are used are selected from the group consisting of palmitic and stearic acid and combinations thereof.

The fatty acid composition can be determined by gas-liquid chromatography (GLC) using the Fatty Acid Methyl Ester (FAME) method, described by the American Oil Chemists' Society, AOCS method Ce 1-62.

The triglyceride oils may contain at least 90% by weight of triglycerides, such as more than 95% by weight. Also, the content of triglycerides in the palm oil fraction may be 99% by weight or more. The purity can be checked by conventional chromatographic methods, such as thin-layer chromatography or high-performance liquid chromatography. The lipid composition in terms of triglycerides, diglycerides, monoglycerides and free fatty acids can be determined by chromatography. A standard method is described by the American Oil Chemists' Society (AOCS), AOCS method Cd 11c-93.

The production of lipids on industrial scale is well known and incorporated into daily practice, and also extensively described in the open literature, for instance in The Lipid Handbook: Edited by D. Gunstone, John L. Harwood, Fred B. Padley; Edition: 2, Chapman and Hall, CRC Press, 1994. Mono- and diglycerides generally are made from the parent triglyceride and glycerol by heating the triglyceride/glycerol mixture with a trace amount of a catalyst such as for instance sodium hydroxide. The resulting mixture contains mono- and diglycerides. Monoglycerides are then obtained through for instance distillation. Free fatty acids are obtained through a similar process by chemical hydrolysis in the presence of water and a catalyst.

In yet another aspect a lipid in a method according to the invention is a free fatty acid, i.e. a fatty acid free from glycerol or freed from glycerol. In yet another aspect a lipid in a method according to the invention is the salt of a free fatty acid.

Crystal formation by lipids is especially noticed for monoglycerides, in particular monoglycerides based on saturated fatty acids comprising at least 16 C atoms and free saturated fatty acids or the salt form of the free saturated fatty acid. The invention therefore provides a method for inducing satiety in a human or animal comprising administering to said human or animal an effective amount of a composition comprising a lipid of which at least part is in a crystal form in the small intestine, wherein said lipid is a monoglyceride or a free fatty acid or a salt of a free fatty acid.

The fatty acid of the monoglyceride or the free fatty acid preferably comprises at least 16 carbon atoms, such as 16, 18, 20, 22 or 24 carbon atoms, i.e. preferably said fatty acid is a C16, C18, C20, C22 or C24 fatty acid. In one of its aspect, the invention provides method for inducing satiety in a human or animal comprising administering to said human or animal an effective amount of a composition comprising a lipid of which at least part is in a crystal form in the small intestine, wherein said lipid comprises at least one $C_{16}$ or higher fatty acid (i.e. a fatty acid with at least 16 carbon atoms). In case of a triglyceride or a diglyceride at least one of the fatty acid chains is $C_{16}$ or higher.

Further preferred is a saturated fatty acid, i.e. a lipid having no double bonds between the carbon atoms of the fatty acid chain; as a consequence the carbon atoms are a fully saturated with hydrogen atoms.

In yet another aspect the invention provides a method for inducing satiety in a human or animal comprising administering to said human or animal an effective amount of a composition comprising a lipid of which at least part is in a crystal form in the small intestine, wherein said lipid comprises at least one saturated fatty acid. In case of a triglyceride or a diglyceride at least one of the fatty acids is saturated.

In an even more preferred embodiment, the free fatty acids or the fatty acids present in triglycerides, diglycerides and/or monoglycerides are C16 or higher and are saturated, i.e. a C16 or higher saturated fatty acid.

Even more preferred, the used lipid comprises at least one fatty acid chain of 16 carbon atoms and is saturated. Suitable examples are triglycerides and diglycerides comprising at least one palmitic acid (with 16 carbon atoms) or stearic acid (with 18 carbon atoms). A preferred monoglyceride comprises palmitic or stearic acid as a fatty acid chain. A preferred free fatty acid is a saturated C16:0, C18:0, C20:0, C22:0 or C24:0 fatty acid. The indication ':0' herein and herein after means that zero unsaturations are present, i.e. 16:0 denotes saturated palmitic acid and C18:0 denotes saturated stearic acid. The indication ':1' means that a single unsaturated carbon-carbon bond is present in the (free) fatty acid and ':2' means that two unsaturated carbon-carbon C—C bonds are present in the (free) fatty acid.

A further preferred embodiment comprises the use of triglycerides that have the saturated fatty acid of 16 carbon atoms or longer on the sn1 or the sn3 position, i.e. one of the outer carbon positions, of the glycerol moiety. On the sn2 position, i.e. the middle carbon position, of the glycerol moiety preferably an unsaturated fatty acid or a shorter fatty acid (14 carbon atoms or less) is attached. Preferably, the used lipid is a vegetable lipid, i.e. a lipid of vegetable origin.

In yet a further preferred aspect, the used lipid is solid at ambient to body temperature. With the phrase "having a solid fat content at ambient to body temperature" it is meant that there should be a solid fat content in the whole interval between ambient and body temperature. The meaning of "a solid fat content" is known to the skilled person and may be determined using standard methodology. Expressed in another way, the term means that there should be at least a residual and detectable solid fat content at body temperature. Residual and detectable solid fat contents may be in the order of more than 0.1 w/w %, such as 0.5 w/w %, 1 w/w %, 2 w/w %, 3 w/w %, 5 w/w %, 10 w/w % or more. Solid fat content may be determined by a benchtop NMR, such as a Brucker Minispec, using ISO 8292 or IUPAC 2.150 methods. These methods yield a melting curve from which it can be easily determined whether a given lipid composition has a solid fat content in the range of ambient to body temperature. Additional methods for determining solid fat content include AOCS methods: AOCS Cd 16b-93 revised in 2000; Direct Method; and AOCS Cd 16-81 revised in 2000, Indirect Method.

Ambient temperature is used to indicate approximate room temperature being the temperature wherein the composition is used according to the invention. Usually this is approximately 20° C., such as 18, 19, 20, 21 or 22° C.

Body temperature differs slightly from species to species, herein this term is used to indicate the body temperature of the human individual or animal to be treated. Usually this is approximately 37° C., such as 36, 36.5, 37, 37.5, 38, 38.5 or 39° C.

In yet another embodiment, the invention provides a method for inducing satiety in a human or animal comprising administering to said human or animal an effective amount of a composition comprising a lipid of which at least part is in a crystal form in the small intestine, further comprising administering an emulsifier. The used lipid and emulsifier can be administered separately within a short time from each other, for example within 10 minutes from each other. More preferably the composition comprising said lipid and said emulsifier are administered within 9, 8, 7, 6, 5, 4, 3, 2, 1 or 0, 5 minutes from each other. Said lipid and said emulsifier are preferably administered at the same time. It is further possible to prepare a composition, such as an oil-in-water emulsion, from said lipid and said emulsifier, and administer the composition (i.e. the emulsion) to a human or animal. Alternatively a dispersion may be prepared from said lipid and said emulsifier and this dispersion may be administered to a human or animal.

It is known from the literature that the good emulsifiers are capable of promoting the formation of crystals of lipid components from emulsion droplets, (Boode and Walstra, 1993). Although proteins can act as good stabilisers of an emulsion, these will not be capable of promoting crystal formation. Therefore it is part of the invention that the lipid composition is in the presence of a good emulsifier once it is subjected to gastro-intestinal lipolysis. A good emulsifier within the context of the present invention includes that the emulsifier may stimulate formation of lipid crystals from an emulsion once it is subject to gastro-intestinal lipolysis. The crystal may grow from the lipid droplet into the aqueous phase.

Any emulsifier may be used in a method according to the invention, however, food emulsifiers are preferred. Food emulsifiers are emulsifiers commonly used in food applications and are generally esters composed of a hydrophilic and a lipophilic part. In general, the lipophilic part comprises stearic, palmitic, oleic, linoleic acid, or linolenic acid or a combination of said fatty acids. The hydrophilic part generally comprises hydroxyl, carboxyl, oxyethylene groups, sugars, carbohydrates, phosphatidylcholines or -ethanolamines.

Examples of families of food-grade emulsifiers are lecithins, mono- and diglycerides, propylene glycol monoesters, acetic acid esters of mono- and diglycerides, lactic acid esters of mono- and diglycerides, citric acid esters of mono- and diglycerides, tartaric acid esters of mono- and diglycerides, mono- and diacetyl tartaric acid esters of mono- and diglycerides, polyglycerol esters, sodium or calcium stearoyl lactylate, sorbitan esters, ethoxylated esters, polysorbates, succinylated esters, fruit acid esters, phosphated mono- and diglycerides and sucrose esters. An emulsion of a lipid can also be obtained when the lipids are mixed with suitable foods or food products, making use of the inherent emulsification properties of said foods or food products or components within that food or food product. Food emulsifiers as used in a method of the invention may be able to emulsify more than 20% by weight of the lipids based on the total weight of lipids, preferably more than 40 w/w %, giving a dispersion, preferably an emulsion which is still liquid in order to facilitate the processing of a food product in which the dispersion, preferably the emulsion may be incorporated.

A preferred emulsifier of the invention is lecithin, for instance produced from egg yolk, milk, soybean oil, sunflower oil or rapeseed oil, which consists of a mixture of mainly phospholipids, such as phosphatidylcholine, phosphatidylethanolamine, phosphatidylserine and phosphatidic acid, and their lyso-phospholipid equivalents. Lecithin refers in this context to crude mixtures of said phospholipids which are obtained on degumming of crude vegetable oils, and which are commercially available as food emulsifiers. Another preferred emulsifier of this invention is formed by the class of polysorbates (polyoxyethylene sorbitan esters, also known under the trade name Tween, e.g. Tween 80 by Roche, Germany), as well as the class of mono- and diglycerides derivatised with food grade acid such as lactic acid, citric acid, tartartic acid, or diacetyl tartaric acid.

A particularly preferred emulsifier is a galactolipid-based emulsifier or a derivative thereof. Thus, an emulsifier for use in a method according to the invention may comprise one or more galactolipids. Galactolipids belong to the group of glycolipids, well known constituents of plant cell membranes. The most important classes of these contain one to four sugars linked glycosidically to diacylglycerol or a monoacylglycerol. The two most abundant classes contain one and two galactose units, respectively, and the commonly used nomenclature and abbreviations of these are mono- and digalactosyldiglyceride (MGDG and DGDG) or mono- and digalactosylmonoglyceride (MGMG and DGMG), sometimes referred to as galactolipids. Galactolipids, primarily DGDG and DGDG-rich materials, have been investigated and found to be a surface active material of interest in industrial applications such as food, cosmetics, and pharmaceutical products. Galactolipid emulsifiers are described in WO 95/20943 and WO 97/11141. Preferred sources for the galactolipid emulsifiers are cereals and grains, particularly oats. Preferably, the source for the galactolipid emulsifier is fractionated oat oil.

In an aspect of the invention, the invention provides a method for inducing satiety in a human or animal comprising administering to said human or animal an effective amount of a composition comprising a lipid of which at least part is in a crystal form in the small intestine, further comprising administering an emulsifier selected from lecithins, galactolipid-based emulsifier or a derivative thereof or mixtures thereof.

A preferred aspect of the invention is the use of a composition wherein galactolipids used in a method according to the invention are combined with palm oil, fractionated palm oil and/or all the other oil combinations mentioned above. For example, a composition suitable for use in a method of the invention can comprise a triglyceride, a diglyceride, a monoglyceride, a free fatty acid or a salt of a free fatty acid (or a combination of any of these) with palm oil or fractionated palm oil.

Furthermore, particularly good results were obtained when a fractionated oat oil was used as a galactolipid-based emulsifier. The invention therefore also relates to the use of a composition wherein the galactolipid-based emulsifier is a fractionated oat oil.

Oil-in-water emulsions of a lipid and an emulsifier may be prepared by using the emulsifier either alone or in combination with other amphiphilic compounds, such as co-surfactants. The oil-in-water emulsion may also comprise optional additives known in the art for improving different aspects of the composition, such as flavouring agents, sweeteners, colorants, thickening agents, preservatives, antioxidants, etc.

Oil-in-water emulsions may be prepared by conventional methods. For example, a 30 wt % emulsion of lipid in water is prepared by adding the emulsifier to said lipid. The continuous phase may be pure water or an aqueous solution containing water-soluble additives such as isotonic agents, sweeteners, flavours, and preservatives. If necessary, the pH of the aqueous phase is then adjusted. The oil phase as well as the aqueous phase is preheated and then the oil phase is added to the aqueous phase under high-shear mixing. The pre-emulsion may then be subjected to high-pressure homogenisation. Alternatively the emulsifier can be dispersed in the aqueous phase after which the oil phase is added under high shear, optionally followed high pressure homogenisation.

It should be emphasized that the emulsifying capacity of the emulsifier depends on the nature or properties of the emulsifier. The fractionated oat oil mentioned above can without further purification be used as an emulsifier in an amount of 1-20% by weight of the total composition for preparing an oil-in-water emulsion of 5-60% by weight of triglycerides. The galactolipid emulsifier of WO 95/20943 should be used in 0.1-5.0% by weight of the total composition for preparing an oil-in-water emulsions of 5-80% by weight of triglycerides.

The amount of fatty acids with at least 16 saturated carbon atoms in a lipid composition used in a method according to the invention can vary. Preferably, the amount of fatty acid with at least 16 saturated carbon atoms is at least 45 w/w % based on the total amount of fatty acids present in said composition, i.e. the invention provides a method for inducing satiety in a human or animal comprising administering to said human or animal an effective amount of a composition comprising a lipid of which at least part is in a crystal form in the small intestine, wherein said C16 or higher saturated fatty acid is present in an amount of at least 45 w/w % based on the total amount of fatty acids in said composition. More preferably, the amount is 46, 47, 48, 49, 50, 55, 60, 65, 70, 75, 80, 85, 90, 91, 92, 93, 94, 95, 96, 97, 98, 99 or even 100 w/w %. The skilled person is well aware how to obtain such lipid composition. For example, one can obtain food grade palmitic acid or stearic acid.

The invention provides a method for inducing satiety in a human or animal comprising administering to said human or animal an effective amount of a composition comprising a lipid of which at least part is in a crystal form in the small intestine, wherein the lipid comprises palmitic acid (i.e. C16: 0) or stearic acid (i.e. C18:0) or a combination thereof.

The invention provides a method for inducing satiety in a human or animal comprising administering to said human or animal an effective amount of a composition comprising a lipid of which at least part is in a crystal form in the small intestine, wherein the lipid comprises at least 45 w/w % palmitic and/or stearic acid.

If the lipid comprises both palmitic acid and stearic acid the weight ratio between these two fatty acids may vary. For example a ratio of palmitic acid:stearic acid, of 10:90, 20:80, 40:70, 40:60, 50:50, 60:40, 70:30, 80:20 or 90:10 may be used.

A lipid used in a method according to the invention can already comprise a certain amount of its fatty acids in a crystal formation. For example, crystals of palmitic acid can be obtained by heating preferably food grade palmitic acid to above its melting point and dispersed in water or in an aqueous substance, preferably under high shear mixing. The dispersion can subsequently be subjected to homogenisation. Finally, the palmitic acid dispersion is allowed to cool down. The resulting product will comprise palmitic acid crystals. In another preferred embodiment the palmitic acid is dispersed in combination with a good emulsifier like a galactolipid-rich lipid fraction to form crystals in the here above mentioned method.

In another example crystals of stearic acid can be obtained by heating preferably food grade stearic acid to above its melting point and dispersed in water or in an aqueous substance, preferably under high shear mixing. The dispersion can subsequently be subjected to homogenisation. Finally, the stearic acid dispersion is allowed to cool down. The resulting product will comprise stearic acid crystals. In another preferred embodiment the stearic acid is dispersed in combination with a good emulsifier like a galactolipid-rich lipid fraction to form crystals in the here above mentioned method.

By a similar method a combination of a palmitic acid and stearic acid crystals can be obtained, for example by using as a starting material a combination of food grade palmitic acid and food grade stearic acid. In a preferred embodiment, the invention provides a method for inducing satiety in a human or animal comprising administering to said human or animal an effective amount of a composition comprising a lipid of which at least part is in a crystal form in the small intestine, wherein at least part of the administered lipid is in a crystal form before administering. In yet another aspect, the administered lipid is not in its final crystal form in which it will be present in the gastro-intestinal tract. During transit through the gastro-intestinal tract the lipid may be subject to (partial) lipolysis, and as a result a different lipid constituent is formed from the ingested lipid composition. The newly formed lipid is more prone to form crystals that are poorly soluble in the mixed micelles in the small intestine—the micelles that facilitate transport of lipids to the intestinal wall. In such a case an emulsifier is preferably also added, because the presence of an emulsifier may facilitate the formation of lipid crystals in the gastro-intestinal tract.

In yet a further aspect a composition comprising a lipid, optionally in combination with an emulsifier, is provided to a human or animal before, at the same time or after a food, feed or beverage is provided to said human or animal. The terms "before" and "after" refer to a time range when compared to said food, feed or beverage of approximately 0.1 to 180 minutes. In other words, a lipid, and optionally an emulsifier, is provided 0.1 to 180 minutes before or 0.1 to 180 minutes after said human or animal has been provided with a feed, feed or beverage. More preferably the time difference is between 0.1 to 60 minutes, 0.1 to 30 minutes, 0.1 to 15 minutes, 0.1 to 10 minutes or 0.1 to 5 minutes.

In an aspect of the invention, the invention provides a method for inducing satiety in a human or animal comprising administering to said human or animal an effective amount of a composition comprising a lipid of which at least part is in a crystal, wherein said lipid comprises at least palmitic acid or stearic acid or a combination thereof.

The invention therefore provides a method for inducing satiety in a human or animal comprising administering to said human or animal an effective amount of a composition comprising a lipid of which at least part is in a crystal form in the small intestine, wherein said composition is administered before, concomitantly with or subsequent to a food, feed or beverage product. In this embodiment, the lipid is provided as a supplement comprising the lipid of which at least part is in a crystal form in the small intestine. Such a supplement can be a liquid or solid composition. A suitable example of a liquid supplement is a small volume of a lipid emulsion or dispersion in water, packed for example in a cup, a mini cup or a sachet. A suitable example of a solid supplement is a tablet or spray-dried powder. The supplement being suitable for human or animal consumption may also be referred to as food supplement or feed supplement herein and herein after.

An example of a suitable food, feed or beverage is a dairy product, including but not limited to yoghurt, milk, cheese, sour cream, milk powder, butter, dairy alternatives, ice cream, margarine, spread, dip, dressing or sauce, processed meat product, confectionary, filling, soup, fruit drink, tea or coffee-based drink, soft drink, near-water, beverages comprising maximum 35% dairy and/or lactic contents by volume, coffee creamer, dessert, chocolate, candy or other confectionary, baked good, nutrition bar, cereal bar, protein-based bar, pasta product and other cereal product, breakfast cereal or muesli, custard, meal replacement product. Optionally the suitable food is combined with other methods to induce satiety such as certain fibres.

As described above, a composition comprising a lipid—optionally in combination with an emulsifier—can be provided together with a food, feed or beverage. This can be performed by providing said food, feed or beverage and said lipid as two separate items and administering them at the same time or by incorporating said lipid into a food, feed or beverage.

The invention thus also provides a method for inducing satiety in a human or animal comprising administering to said human or animal an effective amount of a lipid—optionally in combination with an emulsifier—of which at least part is in a crystal form in the small intestine, wherein said composition is part of a food, feed, beverage or supplement.

A method as described herein may be used during or after a period of weight loss. Such weight loss may have been accomplished by treatment intervention or by an individual's own efforts. Typically, the term "weight loss" refers to achieving a weight loss of at least about 2% of initial or baseline body weight, such as at least about 3%, at least about 4%, at least about 5%, at least about 7%, at least about 10% or even at least about 15%. Such weight loss may be achieved over a period of from, for example, one, two or three to five, six, ten, eighteen or more weeks. Alternatively, weight loss may also be expressed as losing 2 or more body mass index (BMI) points over the period set out above. A method for inducing satiety as described herein is typically used together with or subsequent to a weight reduction or weight maintenance programme. An individual using a method according to the invention may be subject to a dietary regime which results in a negative energy balance. That is to say, a method according to the invention may take place, wherein the individual is subject to negative energy balance. Energy balance is defined as energy intake minus energy output. An individual is described as being in negative energy balance in the event that energy intake is insufficient to meet the requirements of maintenance and production. Hence, an individual in negative energy balance is one wherein calorie intake (from food and drinks) is less than calorie expenditure (through metabolism and energy expended during daily activities).

An individual is in neutral energy balance when the energy intake is approximately equal to the energy output. For the purposes of this invention, an individual subject to a negative energy balance may be at any degree of negative energy balance. Typically, the individual will be in negative energy balance as determined on a daily basis, although an individual may be in negative energy balance for the purposes of this invention as determined over a period of time longer or shorter than one week, for example over a period of about 12 hours or over a period of about 1 week, about two weeks, about 6 weeks or longer, preferably for the entire period that the mixture described herein is consumed.

An individual subject to negative energy balance may be one in which the energy intake is about 90% or less, about 80% or less, about 70% or less, about 60% or less or about 50% or less than the energy intake required to achieve a neutral energy balance.

The calorie intake required to maintain a neutral energy balance will vary according to a wide number of variables. However, the recommended calorie intake for a woman leading typical moderately active lifestyle is in the region of from about 2000 to about 2200 kilocalories per day. The figure for a moderately active man is from about 2500 to about 2800 kilocalories per day. These figures may though need to be adjusted for age, for example old (over about 70 years old) or young (under about 10 years old) individuals generally require a lower energy intake to achieve a neutral energy balance. Also, very active individuals are likely to require a higher energy intake to achieve a neutral energy balance. A dietician will be able to advice as to the approximate energy intake required to achieve a neutral energy balance (and, therefore, the energy intake required to achieve a specific, desired degree of negative energy balance).

Accordingly, for the purposes of this invention, an individual may be generally considered in negative energy balance if they consume less than from about 2000 to about 2200 kilocalories per day (for a female) or less than from about 2500 to 2800 kilocalories per day (for a male). However, individuals consuming more than these energy amounts may, nevertheless, be in negative energy balance depending on their specific circumstances.

Such a dietary regime, where an individual is in negative energy balance or a weight reduction programme, may be referred to as a Low Calorie Diet (LCD). A diet which achieves an energy intake of 800 kcal or less is defined as a Very Low Calorie Diet (VLCD). Individuals using a mixture according to the invention may be subject to a LCD or VLCD.

The Swedish Food Administration advises that three meals are taken each day along with 1 to 3 snacks in order to achieve neutral energy balance. The distribution of energy is recommended to be as follows: breakfast—from about 20% to about 25%; lunch—from about 25% to about 35%; and dinner—from about 25% to about 35%. This suggests that energy intake at lunch may be from about 500 kcal to about 770 kcal (women) and from about 625 kcal to about 890 kcal (men). Negative energy balance may thus be achieved by reducing the energy intake at one or more meals, for example lunch (with reference to the energy amounts set out above) and/or dinner and/or breakfast, whilst maintaining a normal (neutral) energy intake for the remaining meal or meals.

An individual subjected to a method according to the invention may be subject to a meal replacement regime. That is to say, a method according to the invention may be carried out, wherein the individual (i.e. a human or animal) is subject to a meal replacement regime, i.e. is using a meal replacement product. This may be a convenient way in which a negative energy balance may be achieved. In such regimes, meal replacements, for example in the form of a liquid product or a solid bar, are consumed by the individual in place of one, two or more regular daily meals. In addition, the dieter may consume one, two or more meals of real food (which may be calorie-controlled, for example providing from about 400 kcal to about 600 kcal per day). Some liquid diet programs offer pre-packaged meal-options for these "real" meals. Meal replacement products contain typically from about 100 to about 400 kcalories, for example from about 150 to about 250 kcal. They may contain at least about 25% protein and at least about 3 vitamins and minerals. Most commercially-available products contain around 2 to 10 g fibre.

Such a diet may typically provide a total energy intake of from about 1000 kcal to about 1500 kcal per day, for example from about 1200 kcal to about 1400 kcal per day.

An individual subjected to a method of the invention may be subject to a VLCD. This is defined medically as a diet of 800 kcal per day or less. VLCDs are formulated, nutritionally complete, liquid or solid meals. VLCDs also contain the recommended daily requirements for vitamins, minerals, trace elements, fatty acids and protein. The VLCD products are usually a powder which is mixed with water, juice, or other low calorie liquid. Such diets are typically undertaken with medical supervision.

A method of the invention may be used to aid compliance with a meal replacement regime, a LCD or VLCD. This is because the lipid used in a method according to the invention causes a subsequent meal replacement, LCD or VLCD product to induce or reinforce a feeling of satiety such that the individual may more readily tolerate the lower level of energy delivered by the meal replacement product, the LCD or VLCD. By aiding compliance is meant that an individual consuming the mixture in the context of a meal replacement regime, an LCD or VLCD may maintain that regime over a longer period of time (than would be the case for an individual who does not consume the mixture in combination with the meal replacement regime, an LCD or VLCD).

Accordingly, the invention provides a method for inducing satiety in a human or animal comprising administering to said human or animal an effective amount of a lipid of which at least part is in a crystal form in the small intestine, wherein said human or animal is subject to a negative energy balance and/or wherein said human or animal is subject to a meal replacement regime, a weight reduction programme or a weight maintenance programme.

A lipid used in a method according to the invention may be taken daily for a period of for at least 1 week, at least 2 weeks, at least 4 weeks, at least 8 weeks, at least 12 weeks, at least 16 weeks or longer. The aim of the invention may be achieved when the lipid is taken for a single time period or for multiple time periods interspersed with periods of a diet in which the mixture is not taken, for example a diet of neutral energy balance.

In yet another embodiment, the invention provides a composition comprising a lipid of which at least part is in a crystal form or capable to form crystals. For example, the amount of lipid is at least 0.5 gram crystalline lipid composed of C16:0 and higher saturated free fatty acids (optionally in combination with a suitable emulsifier), that passes in this state through the stomach into and through the small intestine. In yet another example, the amount is at least 1 gram of C16:0 or higher saturated fatty acid in any kind of lipidic constituent—triglyceride, diglyceride, monoglyceride or free fatty acid or a salt of a free fatty acid (optionally in combination with a suitable emulsifier) that is in a crystal form before entering the gastro-intestinal tract or is converted into a crystal form during transit in the gastro-intestinal tract.

As described above, the type of lipid can be diverse and is for example a triglyceride, a diglyceride, a monoglyceride or a free fatty acid or a salt of a free fatty acid. The invention thus provides a composition comprising a lipid of which at least part is in a crystal form, wherein said lipid is a triglyceride, a diglyceride, a monoglyceride or a free fatty acid or a salt of a free fatty acid. The above described features of the used lipid are equally well applicable to this part of the invention.

Such a composition can be provided as such (i.e. as a supplement) or incorporated or added to a food, feed or beverage. The used lipid preferably comprises (or is) a saturated fatty acid with at least 16 carbon atoms. In a preferred embodiment, the C16 or higher saturated fatty acid is obtained from palm oil or palm stearine. Palm oil contains approximately 45 w/w C16:0+C18:0 and palm stearine contains approximately 60 w/w C16:0 and higher.

More preferably, such a composition comprises at least 50, 55, 60, 65, 70, 75, 80, 85, 90, 95 w/w % or even higher percentages of C16:0 or higher saturated fatty acids.

The invention further provides A composition comprising a lipid of which at least 45 w/w % of the fatty acids is a C16 or higher saturated fatty acid.

The invention further provides A composition comprising a lipid of which at least 45 w/w % of the fatty acids is a C16 or higher saturated fatty acid, wherein said lipid comprises at least palmitic acid or stearic acid or a combination thereof.

An another aspect the invention provides a composition comprising a lipid of which at least 45% by weight of the fatty acids is a C16 or higher saturated fatty acid, wherein said lipid is obtained from, optionally fractionated, palm oil, palm stearine or shea butter.

The invention further provides a food, feed, beverage or food supplement comprising at least 1 gram of additional lipids comprising at least 45 w/w % C16 or higher saturated fatty acids. Preferably, the food is provided with at least 1.1, 1.2, 1.3, 1.4, 1.5, 1.6, 1.7, 1.8 or 1.9 grams of additional lipids and wherein at least 45 w/w % of said lipids is or comprises a C16 or higher saturated fatty acids. The invention also provides a food, feed, beverage or food supplement comprising at least 2 grams of additional lipids comprising at least 45 w/w % C16 or higher saturated fatty acids.

An additional lipid herein is a lipid that was not originally present in the food, feed or beverage ingredients but which has been added as an additional ingredient.

As outlined above, a method according to the invention is preferably a cosmetic or a non-therapeutic method. However, the knowledge of the current inventors can also be used in a method of treatment. The invention therefore also provides use of a lipid of which at least part is in a crystal form in the small intestine in the preparation of a medicament for treating or preventing obesity, overweight, cardiovascular disease and/or diabetes. Or alternatively worded, the invention also provides a method for treating a human or animal suffering from obesity, overweight, cardiovascular disease and/or diabetes comprising administering to said human or animal an effective amount of a lipid of which at least part is in a crystal form in the small intestine.

In yet another embodiment the invention provides a method for preparing a food, feed, beverage or food supplement product comprising adding to or incorporating into said food, feed or beverage a composition as described above, preferably in combination with an emulsifier. In principle, such a composition comprises a lipid as described herein and can be added to or incorporated into a vast amount of foods, feeds, beverages or supplements, typically food supplements. In a preferred aspect said food, feed or beverage is a dairy product, dairy alternatives, ice cream, margarine, spread, dip, dressing or sauce, processed meat product, confectionary, filling, soup, fruit drink, tea or coffee-based drink, soft drink, near-water, beverages comprising maximum 35% dairy and/or lactic contents by volume, coffee creamer, dessert, chocolate, candy or other confectionary, baked good, nutrition bar, cereal bar, protein-based bar, pasta product and other cereal product, breakfast cereal or muesli, custard, meal replacement product. Optionally the suitable food is combined with other methods to induce satiety such as certain fibres.

A near-water is lightly flavoured drink with a low calorie content, e.g. less than 20 kcal/100 ml, preferably 10 kcal/100 ml or less. An example of a near-water may be a sugar-free near water drink made with 10% fruit juice. It may also be as tea-based near water drink, such as steam distillation extraction of tea comprising added lemon.

The invention further provides a method for preparing a food, feed, beverage or supplement product comprising adding to or incorporating into said food, feed or beverage a composition as described above, wherein said food, feed or beverage is a satiety enhancing food, feed, beverage or supplement product.

In a preferred embodiment, said food, feed or beverage product has a calorie content in the range of 50-250 kcal per serving.

In yet another embodiment, the invention provides a food, feed or beverage product obtainable by a method for preparing a food, feed, beverage or food supplement product comprising adding to or incorporating into said food, feed, beverage or food supplement a composition as described above.

As described above, a method for inducing satiety in a human or animal comprising administering to said human or animal an effective amount of a lipid of which at least part is in a crystal form in the small intestine can be combined with a meal replacement, a weight reduction programme or a weight maintenance programme.

The invention also provides a kit for inducing satiety or suppressing appetite comprising a meal replacement product and a composition comprising a lipid of which at least part is in a crystal form in the small intestine.

In yet another aspect, the invention provides a weight reduction or a weight maintenance programme comprising providing a composition as described herein or a food, feed, beverage or food supplement product as described herein.

The invention is illustrated by the following examples.

EXAMPLES

Fractionated palm oil was obtained by fractionation of palm oil, for example Akofrite (trade name for a palm oil from Karlshamn, Sweden) may be used. The palm oil was fractionated to specific mixtures of suitable triglycerides, based on the combination of mainly palmitic, oleic, linoleic and stearic esters of glycerol, respectively. Preferably the content of triglycerides in the palm oil fraction should be not less than 99% by weight. The fractionated palm oil had a solid fat content at 20 and 35° C. ($N_{20}$ and $N_{35}$) of 31 and 6%, respectively. Fractionated oat oil used comprised about 20% DGDG, and was prepared from oats in accordance with WO 97/11141.

Example 1

To show the crystal-forming effect of an emulsion combining a fat with a high C16:0 content and an emulsifier in vivo the following experiment was performed.

Single-pass jejunal perfusion studies were performed at the Clinical Research Department, University Hospital, Uppsala, Sweden, using the LOC-I-GUT technique (fully described by Knutson et al. (1989) and Lennernas et al. (1992)). Sixteen healthy volunteers participated in the study, the volunteers had ages of 23 to 36 years (mean 28.0 for men and 27.9 for women) and weighing 66-86 kg (males) and 50-70 kg (females) with a mean BMI of 23.1 (males) and 22.2 (females). The study was blinded to the investigators in that way that neither the staff at the lab, nor the subjects were informed which compound was given at two different study occasions. The study was also performed in a randomised cross-over fashion with at least 5 days wash-out period between study visits. This randomised treatment order ensures proper statistics.

All subjects were on a standardized diet the day prior to the experiment, as they received all food items to be consumed from the institute. The energy and macronutrient level was set according to the Swedish Nutrition Recommendations (SNR) for men and women, respectively, at 20-50 years with normal physical activity (male 2900 Kcal, female 2200 Kcal; En % C/F/P 55/30/15).

After an overnight fast of 10 hrs the LOC-I-GUT® perfusion tube (Synectics Medical, Stockholm, Sweden) was introduced through the mouth and positioned in the proximal part of the small intestine under fluoroscopic guidance (Philips BV 21-S).

In 11 of the 16 subjects samples were obtained from all time periods and from both gastrointestinal sampling sites. In 5 subjects some gastrointestinal samples were missing as those experiments did not last for 180 minutes, or samples could not be obtained. The study of data with multiple measurements within the two treatment groups was performed with the analysis of variance for repeated measurements (ANOVA) (Univariate Mixed Effect Model Approach).

The LOC-I-GUT® perfusion technique set up was as follows: A multi-channel tube is brought into the test object (the volunteer). The tube (Synectics Medical, Stockholm, Sweden) is 175-cm long and is made of polyvinyl chloride with an external diameter of 5.3 mm. It contains six channels and is provided distally with two 40-mm long, elongated latex balloons, placed 10 cm apart, each separately connected to one of the smaller channels. In this study only the distal balloon was inflated to prevent fluid from continuing further down the gastrointestinal tract.

The two wider channels in the centre of the tube are for infusion and aspiration of perfusate. The two remaining peripheral smaller channels are used for administration of marker substances and/or for drainage. At the distal end of the tube is a tungsten weight attached to facilitate passage of the tube into the jejunum. A separate tube obtains gastric suction. The LOC-I-GUT® perfusion tube was positioned in the proximal part of the small intestine of the subject, under fluoroscopic guidance (Philips BV 21-S). Having applied local anaesthesia to the throat with a lidocaine spray (Xylocain 10 mg/dose, AstraZeneca, Sodertälje, Sweden) the LOC-I-GUT® tube was introduced through the mouth. During insertion, a Teflon coated guide wire inside the instrument was used to facilitate the passage of the tube into the small intestine (Amplatz extra stiff wire guide, William Cock Europe NS, Bjaereskov, Denmark). During this study the intestinal segment and the occluding balloon was placed in the proximal part of the jejunum.

The tube was placed at approximately the same position in the intestine in all the subjects, as determined and calibrated with the use of a disc memory with automatic 200 msec shut-off (Image Store, Vas Inc, Manassas, Va., USA) containing the different frames from the performed fluoroscopy. With aid of this disc memory the total fluoroscopic time required for checking the positioning of the tube in the proximal jejunum was always less than 15 s. After finishing each experiment the subjects were once again taken to the fluoroscopy room and the position of the tube at the end of each experiment was determined. This second investigation was performed in order to determine if the tubes during the experiments had passed further down into the intestine. Along with the LOC-I-GUT® perfusion tube, another tube was positioned in the stomach for infusion of the different test substances as well as for obtaining samples from the stomach for different analyses (Salem sump tube, Sherwood Medical, U.K.).

Once the perfusion tube was in place, a balloon was inflated with approximately 26-30 ml of air. The distance from the tip of the gastric tube, where the different food stuffs were infused, and the occluding balloon in the proximal jejunum, where the intestinal juice mixed with the different milk compounds was collected, was approximately 35 cm at the beginning of each experiment.

All gastric fluid was collected and replaced by 20 ml of saline solution, prior to infusion of the yogurt through the gastric tube. After infusion, samples were drawn at regular time intervals. After 30 minutes a gastric sample was taken of about 10 ml and replaced with 10 ml saline solution. At the end of the experiment, after 180 minutes, the total contents of the stomach was retrieved. Over three hours intestinal samples were collected every 30 minutes in vials that were kept at 37° C. All samples obtained were accurately weighed and directly brought to a pH below 3 with 0.1 g 1M HCl solution per gram sample, immediately frozen using liquid nitrogen, and stored at −80° C. until freeze dried. Thereafter, the dried samples were also stored at −80° C. Before lowering the pH with HCl, one drop of sample was kept for microscopy analysis.

For this study two yoghurts products were investigated, one containing milk fat—further mentioned as the reference composition—and the other containing an emulsion of purified palm oil and fractionated oat oil as emulsifier, further mentioned as the active composition. This latter composition was made in the following way.

Preparation of a 42.5 Wt % Emulsion with Purified Palm Oil and Fractionated Palm Oil. (Active Composition Fat)

| Ingredients | wt % |
|---|---|
| Water | 57.5 |
| Fractionated palm oil | 40.0 |
| Fractionated oat oil | 2.5 |

Fractionated palm oil and fractionated oat oil were obtained as described above.

The palm oil was purified by running it over a silica column, the oat oil was obtained after extraction of crude oat oil using ethanol. The palm oil was melted at 50° C. and mixed with the fractionated oat oil. The oil phase and the water were preheated to 65-70° C. and then the oil phase was added to the water under high-shear mixing at 15,000 rpm for 4 min. The pre-emulsion was homogenized at 1000 Bar for 6 cycles at 60° C. (Rannie homogenizer, Model Mini-Lab 8.30 H, APV Rannie, Denmark).

The emulsion is commercially available as Fabuless™, from DSM, The Netherlands.

In earlier studies (WO99/02041) it has been shown that such an emulsion of purified palm oil and fractionated palm oil is a composition having a satiety inducing effect in a human.

A) Yoghurt with Dairy Fat (Reference Composition)

A mixture of commercial (brand Albert Heijn) full fat milk and skim milk (6:1) was pasteurised for 35 min at 83.5° C. It was cooled down to 15° C. and stored overnight. The temperature was set at 43° C. and 176 µl/L of the starter CY222 was added. After about 4.5 hours the pH was below 4.6 and the yoghurt was homogenised at 150 bar using a Rannie lab homogeniser (APV Homogenizers, AS, Albertslund, Denmark). The Cream Flavour (540040H, Givaudan) was stirred into the yoghurt (0.1 g/L). The yoghurt was stored at 4° C. in jars of 150 g. The caloric content of the yoghurt is given in table 1. Two batches were produced in this way for use in the experiment. The mean particle sizes for the two batches were respectively 621/572 nm with 21.6/16.2%>1 µm, determined by LS 13 320 Laser Diffraction Particle Size Analyser by Beckman Coulter, after treating the yoghurt with an EDTA solution at pH 12 (1 part yoghurt on 10 parts EDTA solution) to dissolve the protein.

B) Yoghurt with Active Composition Fat (Active Composition)

1120 g of skim milk was heated to ~45° C. using the microwave. The Active composition (KLB06027) was heated to ~35° C. and 80 g was carefully added to the milk. This mixture was homogenised with the lab mixer type L4RT (Silverson Machines Inc, East Longmeadow, Mass., USA) at 900 rpm for 10 minutes. The pasteurisation and the rest of the process was the same as yoghurt with dairy fat. Two batches were produced in this way for use in the experiment. The mean particle sizes for the two batches were respectively 589/520 nm with 13.8/11.7%>1 μm.

TABLE 1

Composition of yoghurt with active composition and yoghurt with dairy fat

| | Yoghurt with Active composition | | | Yoghurt with dairy fat | | |
|---|---|---|---|---|---|---|
| | Percentage | g/serving | kCal/serving | Percentage | g/serving | kCal/serving |
| Skim Milk | 93.3 | 280 | | 13.3 | 40 | |
| full fat milk | 0 | 0 | | 81 | 243 | |
| Active composition | 6.7 | 20 | | 0 | 0 | |
| water | 0 | 0 | | 5.7 | 17 | |
| total | 100 | 300 | | 100 | 300 | |
| protein | 3.3 | 9.8 | 39.2 | 3.3 | 9.9 | 39.6 |
| carbohydrate* | 3.7 | 11.2 | 44.8 | 3.8 | 11.3 | 45.3 |
| fat | 2.8 | 8.5 | 76.5 | 2.8 | 8.5 | 76.5 |
| Caloric content (kCal) | | | 160.5 | | | 161.4 |

From all samples the lipids were analysed on their composition: Total lipid composition in glyceride classes: tri-, di-, and monoglyceride and free fatty acids MDT method') and fatty acid composition (both the free fatty acid content and the fatty acid content (TAME') of the total lipid composition).

The total lipid composition ('MDT') was determined by high pressure liquid chromatography (HPLC). First the freeze dried samples were extracted: 20 mg homogenized sample was extracted with 1 ml solvent mixture (heptane chloroform 3:1). The solid material was then removed by filtration using 0.2 μm PVDF membranes and 10 μl was injected into a normal phase HPLC (Agilient 1100 liquid chromatograph, Agilent Technologies, Santa Clara, Calif.) equipped with a polar (cyano) column and an Evaporative Light Scattering Detection (ELSD; Sedex 75; Polymer Laboratories Ltd, Shropshire, UK). A gradient of heptane-t-butylmethylether was used as a running medium. Using the calibration line and the program Chromeleon Chromatography Management System (Dionex Corporation, Sunnyvale, Calif.), the components were determined. Values were converted into moles by using average molecular masses calculated according to the fatty acid composition of the test products. Lipids were separated with a normal-phase chromatography system using a gradient of organic solvents. Retention times were determined with commercial samples of known composition.

The fatty acid profile of the whole lipid composition was determined by the FAME method (Fatty Acid Methyl Ester). A sample amount of the crude sample was saponified and esterified to its methyl esters, and as such quantified versus an internal standard of pentadecanoic acid methyl ester. Approximately 30 mg of the sample and 20 mg of pentadecanoate were weighed accurately in a headspace vial. A magnetic stirrer, 1 ml toluene/BHT-solution and 4 ml of 0.5 N NaOH-solution were added to each tube. The vials were closed with a crimp cap and were gently stirred and heated in a heating module for 5 minutes at 100° C. After cooling down, 5 ml of BF3-solution (borontrifluorid-methanol-complex: Merck; 80 1663) was added and the vial was closed again and heated once more for 30 minutes at 100° C. After cooling down, 4 ml of heptane and 5 ml of saturated NaCl-solution was added. After mixing thoroughly, the vial was centrifuged at 3000 rpm during 10 minutes. Gas chromatography analysis was performed using a Hewlett Packard 5890 series 2 GC equipped with a flame ionization detector, a fused silica column (CP-Sil-88), and an injection volume of 1 μL with nitrogen as carrier gas.

The profile of the free fatty acid part of the lipid composition was determined by a FFA method described previously (de Jong C, Badings H T. Determination of free fatty acids in milk and cheese, J High Res Chrom 1990; 13:94-8.).

Samples for microscopy observation were taken after 30 minutes (gastric) and 60 and 180 minutes (jejunal). The samples were observed with a Nikon Eclipse E800 light microscopy with imaging programme Lucia GF on MV 1500. One drop of sample was placed on a microscope slide and covered. This was immediately observed by light microscopy, using the phase contrast mode, mostly with the 40× objective. Swiftly at least 4 images were taken, one from each quadrant from each sample of each test object.

The lipid composition (of all lipids: tri-, di- and monoglycerides and free fatty acids using MDT analysis) and the fatty acid composition are given in the tables below for jejunal samples taken 60 minutes and 180 minutes (MDT analysis only) after infusion of the yoghurt.

From table 2 it can be seen that the free fatty acid is the major lipid component of all jejunal samples. The total lipid levels in the active treatment are significantly ($P<0.05$) higher than in the dairy fat treatment over the whole time period, even though the same levels of lipids were administered for both treatments. This illustrates that the lipids from the active treatment were less absorbed by the human body than for the dairy fat treatment.

This is also illustrated in Table 3 were relative FFA contents are mentioned.

TABLE 2

Mean values of absolute mono- di- and triglyceride and free fatty acid (FFA) amounts (MDT method, in mg) in jejunal samples after 60 or 180 minutes (J60, J180)

| | Time (min) | mg | | | | |
|---|---|---|---|---|---|---|
| | | TG | FFA | 1.3 DG | 1.2 DG | MG |
| Active treatment | J60 | 0.09 | 120.82 | 15.87 | 0.96 | 7.59 |
| | J180 | 0.09 | 22.06 | 1.34 | 0.02 | 0.08 |
| Dairy fat treatment | J60 | 0.10 | 71.29 | 13.41 | 0.16 | 3.01 |
| | J180 | 0.06 | 12.08 | 1.22 | 0.03 | 0.18 |

TABLE 3

Relative mono- di- and triglyceride and free fatty acid (FFA) content
(in wt % based on the weight of the total amounts of lipids (i.e. w/w %))
in jejunal samples after 60 or 180 minutes (J60 J180)

| | Time (min) | wt % | | | | | |
|---|---|---|---|---|---|---|---|
| | | TG | FFA | 1.3 DG | 1.2 DG | MG | sum |
| Active treatment | J60 | 0.1 | 83.1 | 10.9 | 0.7 | 5.2 | 100 |
| | J180 | 0.4 | 93.5 | 5.7 | 0.1 | 0.3 | 100 |
| Dairy fat treatment | J60 | 0.1 | 81.0 | 15.2 | 0.2 | 3.4 | 100 |
| | J180 | 0.5 | 89.0 | 9.0 | 0.2 | 1.3 | 100 |

In table 3 the relative levels of triglycerides, diglycerides, monoglycerides and free fatty acids are given. From the table it can be seen that the majority of the lipids in the jejunum at 60 and 180 minutes consists of free fatty acids for both treatments.

From table 4 it can be seen that the active treatment is considerably enriched in C16:0 and C18:0 and depleted in C18:1 compared to the starting composition, whereas the reference product with dairy fat is not increased (C16:0 FFA versus starting composition, the most abundant compound—see table 3), or somewhat increased (C18:0 FFA) and somewhat decreased in C18:1. The higher lipid levels in the active treatment show up especially as higher palmitic acid levels.

TABLE 4 relative fatty acid composition (w/w %) of lipids found in the
jejunum after 60 minutes and in the starting products

| | | C14:0 | C16:0 | C18:0 | C18:1 | C18:2 | rest | Sum |
|---|---|---|---|---|---|---|---|---|
| Active treatment | | | | | | | | |
| yog | FA | 1.3 | 44.3 | 4.3 | 38 | 10.6 | 1.5 | 100 |
| J60 | FA | 1.1 | 57.4 | 5.9 | 18.9 | 12 | 4.7 | 100 |
| J60 | FFA | 1.3 | 62.2 | 7.5 | 19 | 9.6 | 0.4 | 100 |
| Dairy fat treatment | | | | | | | | |
| yog | FA | 12.8 | 32.8 | 9.9 | 18.8 | 1.5 | 24.2 | 100 |
| J60 | FA | 8.6 | 44 | 14.3 | 14.5 | 7.5 | 11.1 | 100 |
| J60 | FFA | 13.3 | 40.2 | 19 | 16.3 | 6.4 | 4.8 | 100 |

FFA: the free fatty acid content, FA: the fatty acid content of the total lipid composition, and yog: the fatty acid composition of the total lipids in the starting product.

From the microscopy observations the most surprising feature is that in the jejunal samples (60 and 180 minutes) obtained after ingestion of the yoghurt with the Active composition needle-shaped crystals were found in almost all of the samples, whereas in the control with dairy fat, crystals were seen in much less cases. This is also summarised in table 5 below, showing scoring of amounts of crystals seen in light microscopy images per treatment (person).

TABLE 5 scoring of amounts of crystals seen in light
microscopy images per treatment (person)

| | J60 (0) | J60 (+) | J60 (++) | J180 (0) | J180 (+) | J180 (++) |
|---|---|---|---|---|---|---|
| Dairy fat treatment | 9 | 7 | 0 | 11 | 5 | 0 |
| Active treatment | 2 | 7 | 7 | 6 | 3 | 7 |

0 = blank/none
+ = one or a few/possibly
++ = many

A few samples from the jejunum (taken at 60 minutes, after freeze-drying) were subjected to X-ray diffraction to determine the character of the observed crystals. A typical diffraction pattern was seen, which can be explained by crystalline material made up from palmitic acid (refraction at 2θ=21.5 and 24° and smaller peaks at 2θ=7, 10 and 12.5°) and NaCl and KCl (main refraction at 2θ=28°). More specifically the following refractions were assigned for NaCl 2θ=27.3, 31.7, 45.4, 53.8, 56.4°, and KCl 2θ=28.2, 40.4, 50.1°. However crystals observed by light microscopy will not be NaCl or KCl crystals as these will be dissolved in the main aqueous phase of the jejunum.

Also a set of dried samples were subjected to DSC (Differential Scanning calorimetry Mettler Toledo DSC 821) with the following settings: Temperature range: −15 to 200° C.; Rate: 5° C./min.; Reference: Empty Al-40 pan; Sample: ca. 10 mg in Al-40 pan. The samples obtained from the jejunum after consumption of the active composition showed a melting temperature (peak value) of 58° C. and dried jejunal samples from treatment with the reference (dairy fat) composition showed a melting temperature of around 52° C. The melting temperature of 58° C. of the samples of the active composition is close to the value of pure palmitic acid of 63° C., whereas Sodium palmitate melts at 270° C.

Objects with crystalline features were also analyzed with Raman microscopy. Raman Microscopy was performed on freeze-dried material using a Jobin Yvon LabRAM HR800 system (600 grooves/mm grating and A=514.5 nm laser). An Olympus LM PIanFL objective (100×) was used in conjugation with a 100 μm confocal pinhole.

The Raman spectrum obtained from a spot where crystalline object was identified by light microscopy, was compared to recorded reference spectra of palmitic acid, sodium and calcium palmitate. The signals of the crystalline object were attributed to palmitic acid.

Overall it can be concluded that the active treatment using the active compositions generates many crystals in the gastrointestinal tract, and the reference product only relatively few.

Combined with the relatively high levels of (free) palmitic acid (C16:0) and stearic acid (C18:0) and the physical characteristics it is concluded that the crystals are composed of palmitic and stearic acid.

Example 2

In the following test, yoghurts with triglycerides high in C16:0 in combination with an emulsifier were subjected to an in-vitro treatment, using a model gut set up as was developed by TNO, Zeist, the Netherlands, generally referred to as the TNO Intestinal Model, TIM. This in-vitro gastrointestinal model simulates the successive dynamic processes in the stomach, the small intestine and in the large intestine. The model is a unique tool to study the stability, release, dissolution, absorption and bioconversion of nutrients, chemicals, bioactive compounds and pharmaceuticals in the gastrointestinal tract. It is further discussed for instance by Minekus (Minekus, M. (1998) and Minekus, M.; Marteau, P; Havenaar, R.; Huis in 't Veld, J. H. J., ATLA Antern. Lab. Anim. 1995, 23, 197-209).

The TIM simulates the successive dynamic conditions in the gastric-small-intestinal tract, such as body temperature, the pH curves, concentrations of electrolytes, and the activity of enzymes in the stomach and small intestine, the concentrations of bile salts in the different parts of the gut, and the kinetics of passage of the chyme through the stomach and small intestine, and the absorption of low molecular molecules and water. Material (food) is passed through a sequence of modules mimicking the effect of transit through consecutively the stomach, the duodenum, the jejunum and the ileum. At two points hollow fiber semi-permeable membranes mimic the passage of digested material over the intestinal wall. At specific points gastro-intestinal juices are added: gastric juice (lipase and pepsin) in the stomach compartment, and sodium bicarbonate solution and pancreatin and bile in the duodenal compartment.

Two yoghurt products were made; the procedure to make yoghurt was the same way as described in example 1. A yoghurt (A) comprising 5.88 wt % of an 42 wt % lipid-containing emulsion (Fabuless™), as described in example 1 corresponding to 2.5 wt % total lipids. And a yoghurt B which was a mixture of two yoghurts: a yoghurt with finely dispersed oat oil and a yoghurt with finely dispersed palm oil. The yoghurt with the palm oil and the yoghurt with the oat oil were mixed in such a ratio that the overall composition of this mixture was the same as for yoghurt A. However, the microstructure of yoghurt A and yoghurt B differ: in yoghurt A the palm oil surface is covered with oat oil, whereas in yoghurt B the palm oil in yoghurt not covered by the polar lipids from the oat oil but the palm oat and oat oil are separately dispersed. Small size samples (approx. 1 ml) were taken during transit of the test product through the stomach and the small intestine. Samples were taken from the lumen of the stomach compartment (60, 120 and 180 minutes after insertion of the yoghurt into to stomach) and from the jejunum and ileum compartments (60, 120, 180, 240, and 300 minutes after insertion of the yoghurt into the stomach). The luminal samples were visually analyzed under the microscope (phase contrast or bright field 400×). The luminal samples were analysed to determine their triglyceride-diglyceride-monoglyceride and free fatty acid lipid composition. In addition to the lumen samples, filtrate samples were collected from the semi-permeable membranes located at the jejunum and ileum compartments. From the filtrate samples the fatty acid composition was determined, by Gas Chromatography analysis after extraction with KOH/ethanol at 70° C. for 1 h.

From the light microscopy samples obtained from the jejunum and ileum compartments surprisingly almost all contained crystals, usually aggregates of a number of crystals. The crystals are all larger than the oil droplets they originate from. This was found for yoghurt A as well as for yoghurt B where in the beginning the palm oil and the polar oat oil were physically separated.

The lipids of all lumen samples (both yoghurts) consisted mostly of free fatty acids. In the jejunal samples some monoglyceride and triglyceride was seen. The ileal samples were richest in free fatty acid with some triglyceride next to it (not displayed in a Table). The relative fatty acid contents of the lipid compositions of the filtrate samples are summarised in table 6. The four most relevant fatty acids are given. These filtrate samples represent the lipids that were absorbed over the (artificial) intestinal wall. In the second column the gastric intake is given, representing the fatty acid composition of the lipids in the samples that were ingested into the stomach compartment. In the duodenal compartment of the set up also a minor amount of bile was added and that contained also a substantial amount of lipids rich in the four main components in about equal amounts. Table 6 shows that the filtrate samples were highly enriched in C18:1 and C18:2 compared to the starting composition coming partly from the samples and partly from the bile. These samples are however substantially depleted from C16:0 and C18:0, meaning that these saturated fatty acids are not filtered out of the lumen. Hence the material left in the lumen (the non-absorbed lipids) was relatively enriched by these saturated fatty acids.

TABLE 6

| sample | Gastric intake | jejunum filtrate | | | | ileum filtrate | | | |
|---|---|---|---|---|---|---|---|---|---|
| time (min) | 0 | 0-60 | 60-120 | 120-180 | 180-300 | 0-60 | 60-120 | 120-180 | 180-300 |
| yoghurt B | | | | | | | | | |
| C16:0 | 43.5 | 29.4 | 21.2 | 19.4 | 24.2 | 36.0 | 41.0 | 39.9 | 40.2 |
| C18:0 | 5.1 | 12.3 | 6.3 | 5.7 | 9.7 | 16.0 | 7.8 | 7.1 | 8.4 |
| C18:1 | 40.7 | 34.5 | 52.3 | 54.6 | 41.9 | 32.0 | 37.3 | 39.1 | 36.6 |
| C18:2 | 10.6 | 23.8 | 20.2 | 20.3 | 24.2 | 16.0 | 13.8 | 13.9 | 14.8 |
| yoghurt A | | | | | | | | | |
| C16:0 | 43.1 | 30.4 | 22.1 | 20.2 | 25.2 | 33.3 | 21.1 | 18.4 | 20.4 |
| C18:0 | 5.2 | 13.2 | 6.9 | 6.1 | 10.2 | 13.3 | 7.0 | 5.6 | 7.8 |
| C18:1 | 40.0 | 31.7 | 49.6 | 51.9 | 40.6 | 33.3 | 49.7 | 53.8 | 47.9 |
| C18:2 | 11.6 | 24.8 | 21.5 | 21.7 | 24.0 | 20.0 | 22.2 | 22.2 | 24.0 |

It can therefore be concluded that for both yoghurts the luminal samples from both jejunum and ileum contained substantial amounts of crystals and were enriched in C16:0 palmitate and C18:0 stearate, all in free fatty acid form. It is therefore very likely that the observed crystals were built up from these saturated free fatty acids. Moreover this experiment shows that the presence of a good emulsifier, such as an emulsifier comprising galactolipids, during the gastro-intestinal lipolysis may facilitate the formation of these crystals, even if they are ingested in a state physically separated from the triglyceride.

Example 3

Analogous to example 2 four yoghurts with 3.5% fat (lipids) were followed during transit in the TNO intestinal Model (TIM). The gastric small intestinal model TIM is described in literature (40).

The digestion process in the model was monitored for 5 hours. During the first 3 hours, the gastric content was gradually delivered into the small intestine via the Pyloric valve. At the end of the experiment, approximately 80% of the small intestine content was gradually delivered into the Large intestine via the Ileocecal valve.

Gastric secretions consisted of pepsin from porcine gastric mucosa (EC 3.4.23.1; Sigma-Aldrich Canada) and lipase (EC 3.1.1.3, from *Rhizopus oryzae*, Amano Pharmaceuticals, Japan), both dissolved in a Gastric Electrolyte Solution (GES: 3.1 g/l NaCl; 1.1 g/l KCl; 0.15 g/l CaCl2; 0.6 g/l NaHCO3). At the beginning of the experiment, a solution of trypsin from porcine pancreas (EC 3.4.21.4; Sigma-Aldrich Canada) was directly introduced into the duodenum. Also, porcine bile extract (supernatant of centrifuged, thawed bile from frozen, fresh collected porcine bile); pancreatic solution (Pancrex V powder; Paines and Byrne, UK), and intestine electrolyte solution (5.0 g/l NaCl; 0.6 g/l KCl; 0.3 g/l CaCl2 at pH 7.0) were delivered in the duodenal compartment.

Four yoghurts with 3.5% lipids (Fractionated palm oil; Shea stearin; Palmitic acid and dairy fat, respectively) were followed during transit in TIM). Prior to testing the yoghurt containers were gently shaken to homogenise contents. At the beginning of each experiment, a 270 g amount of yoghurt was introduced into the gastric (i.e. stomach)—compartment of the TIM. At specific intervals samples were taken from different compartments of the gastro-intestinal tract (Gastric-; jejunum- and ileum lumen). A selection of fresh lumen samples were also directly visually studied by Bright Field microscope (Leica ATC2000 Binocular Microscope), equipped with a phase contrast mode. After study, microscope samples were stored at −20° C.

All yoghurts were tested in duplicate.
The following lipids (fats) were tested:
a) fractionated palm oil
b) dairy fat, from full fat milk,
c) shea stearin, a triglyceride fraction obtained from shea butter,
d) palmitic acid.
Shea-stearin was obtained from AarhusKarlshamn (AAK). Fractionated palm oil was acquired from Lipid Technologies Provider (LTP). Palmitic acid (90%) was obtained from Aldrich. Fractionated oat oil, which was used as an emulsifier, was obtained from extraction of crude oat oil obtained from Swedish Oat Fibre AB (SOF).

Emulsion Preparation (Fractionated Palm Oil and Shea Stearin)

Fractionated palm oil and fractionated oat oil were obtained as described above. Emulsions were made from fractionated palm oil and shea stearin using fractionated oat oil as emulsifier using a process described in example 1. The following settings were applied: high shear mixing of fats and emulsifier by turrax for 2 min, followed by homogenizing during 4 passes at 600 bar. The emulsion comprising fractionated palm oil is commercially available as Fabuless™, from DSM, The Netherlands.

Palmitic Acid Dispersion Preparation

A dispersion comprising palmitic acid crystals was made by high shear mixing (ultra turrax) of a palmitic acid and fractionated oat oil mixture (ratio: 92.3%/7.7%) in water. The turrax treatment was performed during 15 min at 80° C., and the mixture was slowly cooled to ambient temperature while stirring. The dispersion thus obtained had a 28 wt % lipid content.

Yoghurt Production

Yoghurt fermentation was performed with a non-exo-polysaccharide (EPS) culture (Delvo-Yog CY222 from DSM, the Netherlands) starting with commercial skimmed milk 0% fat; brand Albert Heijn), No extra fat was added during the production of the yoghurt. The yoghurts were not sweetened or flavored. Final lipid content of all yoghurts was 3.5%. This lipid content was reached either by
   introduction of lipid emulsions into skim milk and producing yoghurt from the milk comprising the emulsion (lipids a) and c));
   or starting with a commercial homogenised full fat milk (lipid b)) (3.5% fat; brand Albert Heijn), no extra fat or emulsifiers were added;
   or by adding the dispersion of palmitic acid crystals into a freshly prepared yoghurt (lipid d)) by gentle mixing.

The yoghurts were iso-caloric. The ratio fat vs. protein was made as equal as possible.

The lipid composition of the emulsions or dispersions (fractionated palm oil and fractionated oat oil, shea stearin lipid and fractionated oat oil, palmitic acid and fractionated oat oil, dairy fat as such) as determined by free fatty acid FFA analysis is given in the table 7.

The profile of the free fatty acid part of the lipid composition (FFA analysis) was determined by a method developed by the NIZO. (de Jong C, Badings H T. Determination of free fatty acids in milk and cheese, J High Res Chrom 1990; 13:94-8).

TABLE 7

| | Lipid compositions | | | |
|---|---|---|---|---|
| | Fatty acid w/w % | | | |
| Fatty acid | Fractionated palm oil | Dairy fat | Shea Stearin | Palmitic acid |
| C10:0 | | 3.0 | | |
| C12:0 | | 5.0 | | |
| C14:0 | 1.0 | 14.0 | | 0.9 |
| C16:0 | 42.5 | 34.0 | 3.8 | 90.7 |
| C18:0 | 3.9 | 10.0 | 55.8 | 1.0 |
| C18:1 | 39.8 | 20.0 | 33.2 | 2.7 |
| C18:2 | 11.8 | 2.0 | 5.1 | 3.1 |
| C18:3 | 0.0 | | | |
| C20:0 | | | 1.9 | |
| Ratio* | 0.88 | 1.00 | 1.60 | 13.54 |

*Ratio (C16:0 + C18:0 + C20:0)/(C10:0 + C12:0 + C14:0 + C18:1 + C18:2 + C18:3)

Samples drawn from the jejunum (i.e. jejunum ileum) (at t=60 and 180 minutes after insertion of yoghurt in the stomach compartment) and the ileum (i.e. ileum lumen) (at t=120 and 240 minutes after insertion of yoghurt in the stomach compartment) compartment were observed by light microscopy directly after sample drawing. At least 4 images were taken. The amount of crystals observed in jejunal and ileal samples were estimated qualitatively by human observation, and divided in the following classes:
   0 for no crystals in the at least 75% of the images;
   +: few crystals (max 10), in some or most of the images;
   ++: many (>10) crystals in most or all of the images.
The results are listed in table 8.

TABLE 8

Results of light microscopy observations (minutes after insertion of yoghurt in the stomach compartment).

| | Jejunum lumen | | | Ileum lumen | | |
|---|---|---|---|---|---|---|
| Time (min) | 60 | 180 | Features* | 120 | 240 | Features* |
| Fractionated palm oil | ++ | ++ | Needle shaped crystals and hedgehogs | + | + | needle shaped crystals and hedgehogs |
| Dairy fat | 0/+ | 0/+ | Spherical drops | 0 | 0 | |
| Shea stearin | + | + | Crystals: not needle-shaped, more rounded off, aspect ratio smaller <5 | + | + | hedgehogs, less crystals than in jejunum lumen |
| Palmitic acid | ++ | ++ | needle shaped crystals, aspect ratio smaller <5 | + | + | |

*Hedgehog: aggregate of needle shaped crystals.

The free fatty acid level for all fatty acids in the ileum as well as the saturated fatty acid (FA) fraction C16:0 and C18:0 and higher in the ileum lumen were determined using FFA method as described above.

TABLE 9

Total FFA levels in the ileum lumen versus time (in hours after insertion of yoghurt in the stomach compartment) (average of duplicate measurements) (g FFA/kg dry matter).

| Yoghurt | time (hr) | | | | |
|---|---|---|---|---|---|
| | 1 | 2 | 3 | 4 | 5 |
| Fractionated palm oil | 125.2 | 236.4 | 308.0 | 326.3 | 317.5 |
| Dairy fat | 101.1 | 171.3 | 244.0 | 241.5 | 252.0 |
| Shea stearin | 84.3 | 234.4 | 320.5 | 340.4 | 353.5 |
| Palmitic acid | 171.5 | 348.3 | 504.8 | 461.6 | 466.2 |

TABLE 10 w/w % of saturated FFA (C16:0 + C18:0 + C20:0) based on total FFA in the ileum lumen versus time (average of duplicates).

| Yoghurt | time (hr) | | | | |
|---|---|---|---|---|---|
| | 1 | 2 | 3 | 4 | 5 |
| Fractionated palm oil | 58.4 | 66.0 | 73.7 | 79.5 | 83.7 |
| Dairy fat | 48.4 | 54.6 | 61.1 | 65.7 | 69.5 |
| Shea stearin | 57.9 | 73.5 | 80.9 | 86.7 | 90.3 |
| Palmitic acid | 91.4 | 96.6 | 97.8 | 97.5 | 97.6 |

The yoghurts comprising palmitic acid show the highest amounts of FFA in the ileum lumen, followed by shea butter, than followed by fractionated palm oil, and than followed by dairy fat. A relative enrichment of saturated fatty acids in time is observed, which is most pronounced for palmitic acid, than for shea stearin, than for fractionated palm oil and than for dairy fat. All differences are statistically significant ($P<0.05$).

Objects having crystalline features were analyzed with Raman spectroscopy (as described for example 1). The signals of the crystalline objects may be attributed to free saturated fatty acids and/or to the corresponding salts (i.e. salt of the free saturated fatty acid, such as Calcium palmitate and/or Calcium stearate).

From the FFA and Raman analysis it is believed that the crystals are mainly composed of saturated palmitic acid and saturated stearic acid, possibly as or including their corresponding salts.

REFERENCES

1. Adrian T E, Ferri G L, Bacarese-Hamilton A J, Fuessl H S, Polak J M, Bloom S R. Human distribution and release of a putative new gut hormone, peptide YY. *Gastroenterology* 89: 1070-1077, 1985.
2. Borovicka J, Schwizer W, Guttmann G, Hartmann D, Kosinski M, Wastiel C, Bischof-Delaloye A, Fried M. Role of lipase in the regulation of postprandial gastric acid secretion and emptying of fat in humans: a study with orlistat, a highly specific lipase inhibitor. Gut 46: 774-781, 2000.
3. Buffa R, Solcia E, Go V L. Immunohistochemical identification of the cholecystokinin cell in the intestinal mucosa. Gastroenterology 70: 528-532, 1976.
4. Chapman I M, Goble E A, Wittert G A, Horowitz M. Effects of smallintestinal fat and carbohydrate infusions on appetite and food intake in obese and nonobese men. *Am J Clin Nutr* 69: 6-12, 1999.
5. Cox J E, Kelm G R, Meller S T, and Randich A. Suppression of food intake by GI fatty acid infusions: roles of celiac vagal afferents and cholecystokinin. Physiol Behav 82: 27-33, 2004.
6. Dobson C L, Davis S S, Chauhan S, Sparrow R A, Wilding I R. The effect of oleic acid on the human ileal brake and its implications for small intestinal transit of tablet formulations. Pharm Res 16: 92-96, 1999.
7. Feinle C, O'Donovan D G, Doran S, Andrews J M, Wishart J, Chapman I, Horowitz M. Effects of fat digestion on appetite, APD motility, and gut hormones in response to duodenal fat infusion in humans. Am J Physiol Gastrointest Liver Physiol 284: G798-G807, 2003.
8. Feinle C, Rades T, Otto B, Fried M. Fat digestion modulates gastrointestinal sensations induced by gastric distention and duodenal lipid in humans. Gastroenterology 120: 1100-1107, 2001.
9. Feltrin K L, Little T J, Meyer J H, Horowitz M, Smout A J, Wishart J, Pilichiewicz A N, Rades T, Chapman I M, and Feinle-Bisset C. Effects of intraduodenal fatty acids on appetite, antropyloroduodenal motility, and plasma CCK and GLP-1 in humans vary with their chain length. Am J Physiol Regul Integr Comp Physiol 287: R524-R533, 2004.
10. Geliebter A. Gastric distension and gastric capacity in relation to food intake in humans. Physiol Behav; 44: 665-668, 1988. I
11. Heddle R, Collins P J, Dent J, Horowitz M, Read N W, Chatterton B, Houghton L A. Motor mechanisms associated with slowing of the gastric emptying of a solid meal by an intraduodenal lipid infusion. 1: J Gastroenterol Hepatol.; 4(5):437-47, 1989.
12. Hill J O, Wyatt H R, Reed G W, Peters J C. Obesity and the environment: where do we go from here? Science. 299: 853-855, 2003.
13. Hunt J N and Knox M T. A relation between the chain length of fatty acids and the slowing of gastric emptying. J Physiol 194: 327-336, 1968.
14. Hveem K, Jones K L, Chatterton B E, Horowitz M. Scintigraphic measurement of gastric emptying and ultrasonographic assessment of antral area: relation to appetite. Gut 38: 816-821, 1996.
15. Jones K L, Doran S M, Hveem K, Bartholomeusz F D, Morley J E, Sun W M et al. Relation between postprandial satiation and antral area in normal subjects. Am J Clin Nutr 66: 127-132, 1997.
16. Keller J, Hoist J J, Layer P. Inhibition of human pancreatic and biliary output but not intestinal motility by physiological intraileal lipid loads. Am J Physiol Gastrointest Liver Physiol 290: G704-G709, 2006.
17. Lal S, Kirkup A J, Brunsden A M, Thompson D G, and Grundy D. Vagal afferent responses to fatty acids of different chain length in the rat. Am J Physiol Gastrointest Liver Physiol 281: G907-G915, 2001
18. Lal S, McLaughlin J, Barlow J, D'Amato M, Giacovelli G, Varro A, Dockray G J, and Thompson D G. Cholecystokinin pathways modulate sensations induced by gastric distension in man. Am J Physiol Gastrointest Liver Physiol 287: G72-G79, 2004
19. Layer P, Schlesinger T, Groger G, Goebell H. Modulation of human periodic interdigestive gastrointestinal motor and pancreatic function by the ileum. Pancreas 8: 426-432, 1993.

20. Lin H C, Zhao X T, Wang L. Fat absorption is not complete by midgut but is dependent on load of fat. Am J Physiol 271: G62-G67, 1996.
21. Macintosh C G, Andrews J M, Jones K L, Wishart J M, Morris H A, Jansen J B, Morley J E, Horowitz M, Chapman I M. Effects of age on concentrations of plasma cholecystokinin, glucagon-like peptide 1, and peptide YY and their relation to appetite and pyloric motility. Am J Clin Nutr. 69(5):999-1006, 1999.
22. Matzinger D, Degen L, Drewe J, Meuli J, Duebendorfer R, Ruckstuhl N, D'Amato M, Rovati L, and Beglinger C. The role of long chain fatty acids in regulating food intake and cholecystokinin release in humans. Gut 46: 688-693, 2000.
23. McLaughlin J, Grazia-Luca M, Jones M N, D'Amato M, Dockray G J, and Thompson D G. Fatty acid chain length determines cholecystokinin secretion and effect on human gastric motility. Gastroenterology 116: 46-53, 1999.
24. Pironi L, Stanghellini V, Miglioli M, Corinaldesi R, De Giorgio R, Ruggeri E et al. Fat-induced ileal brake in humans: a dose-dependent phenomenon correlated to the plasma levels of peptide YY. Gastroenterology 105: 733-739, 1993.
25. Read N W, McFarlane A, Kinsman R I, Bates T E, Blackhall N W, Farrar G B et al. Effect of infusion of nutrient solutions into the ileum on gastrointestinal transit and plasma levels of neurotensin and enteroglucagon. Gastroenterology 86: 274-280, 1984.
26. Schwizer W, Asal K, Kreiss C, Mettraux C, Borovicka J, Remy B, Guzelhan C, Hartmann D, Fried M. Role of lipase in the regulation of upper gastrointestinal function in humans. Am J Physiol Gastrointest Liver Physiol 273: G612-G620, 1997.
27. Spiller R C, Trotman I F, Higgins B E, Ghatei M A, Grimble G K, Lee Y C et al. The Ileal brake-inhibition of jejunal motility after ileal fat perfusion in man. Gut 25: 365-374, 1984.
28. Van Citters G W, Lin H C. The ileal brake: a fifteen-year progress report. Curr Gastroenterol Rep 1: 404-409, 1999.
29. Vasan, R S, Pencina, M J, Cobain, M, et al. Estimated risks for developing obesity in the Framingham Heart Study. Ann Intern Med 143:473, 2005.
30. Welch I, Saunders K, Read N W. Effect of ileal and intravenous infusions of fat emulsions on feeding and satiety in human volunteers. Gastroenterology 89: 1293-1297, 1985.
31. Welch I, Saunders K, Read N W. Effect of ileal and intravenous infusions of fat emulsions on feeding and satiety in human volunteers. Gastroenterology 89: 1293-1297, 1985
32. Welch I M, Cunningham K M, Read N W. Regulation of gastric emptying by ileal nutrients in humans. Gastroenterology 94: 401-404, 1988.
33. Welch I M, Sepple C P, Read N W. Comparisons of the effects on satiety and eating behaviour of infusion of lipid into the different regions of the small intestine. Gut 29: 306-311, 1988.
34. WHO. Information from the WHO is available online at www.who.int/nut/obs.htm.
35. Woods S C. Gastrointestinal satiety signals I. An overview of gastrointestinal signals that influence food intake. Am J Physiol Gastrointest Liver Physiol 286: G7-G13, 2004.
36. Xu X, Zhu H, and Chen J D. Pyloric electrical stimulation reduces food intake by inhibiting gastric motility in dogs. Gastroenterology 128: 43-50, 2005.
37. a) Boode K, Walstra, P. Partial coalescence in oil-in-water emulsions 1. Nature of the aggregation; Colloids and Surfaces A: Physicochemical and Engineering Aspects; 81, 13 Dec. 1993, 139-151. b) Boode K, Walstra, P, Groot-Mostert, A E A. Partial coalescence in oil-in-water emulsions 2. Influence of the properties of the fat; Colloids and Surfaces A: Physicochemical and Engineering Aspects; 81, 13 Dec. 1993, 139-151
38. Knutson L, Odlind B, Hällgren R. A new technique for segmental jejunal perfusion in man. Am J Gastroenterol 1989; 84:1278-84
39. Lennernas H, Ahrenstedt Ö, Hällgren R, Knutson L, Ryde M, Paalzow L K. Regional jejunal perfusion, a new in vivo approach to study oral drug absorption in man. Pharmaceutical Research 1992; 9:1243-51
40. Minekus, M. 1998 Development and validation of a dynamic model of the gastrointestinal tract. PhD Thesis, University of Utrecht; Elinkwijk b.v., Utrecht, Netherlands 1998

The invention claimed is:

1. A medicament for treating or preventing obesity, overweight, cardiovascular disease and/or diabetes, wherein the medicament comprises a composition comprising a lipid and an emulsifier, wherein at least 45 w/w % of fatty acids of the lipid are C16 or higher saturated fatty acids, and wherein at least 20 w/w % of the lipid is in a crystal form.

2. The medicament according to claim 1, wherein said lipid comprises at least palmitic acid or stearic acid or a combination thereof.

3. The medicament according to claim 1, wherein said lipid is obtained from palm oil, palm stearine or shea butter, or fractionated palm oil, palm stearine or shea butter.

4. A food, feed, beverage or food supplement comprising at least 1 gram of additional lipids and an emulsifier, wherein at least 45 w/w % of fatty acids of the lipids are C16 or higher saturated fatty acids, and wherein at least 20 w/w % of the lipids are in a crystal form.

5. The food, feed, beverage or food supplement according to claim 4, wherein said lipid comprises at least palmitic acid or stearic acid or a combination thereof.

6. The food, feed, beverage or food supplement according to claim 4, wherein said lipid is obtained from palm oil, palm stearine or shea butter, or fractionated palm oil, palm stearine or shea butter.

7. A weight reduction or a weight maintenance program comprising providing a composition comprising a lipid and an emulsifier to a subject in need of weight reduction or weight maintenance, wherein at least 45 w/w % of fatty acids of the lipid are C16 or higher saturated fatty acids, and wherein at least 20 w/w % of the lipid is in a crystal form.

8. A satiety enhancing food, feed, beverage or food supplement which comprises a composition comprising a lipid and an emulsifier, wherein at least 45 w/w % of fatty acids of the lipid are C16 or higher saturated fatty acids, and wherein at least 20 w/w % of the lipid is in a crystal form.

9. The satiety enhancing food, feed, beverage or food supplement according to claim 8, wherein the lipids comprise at least one selected from the group consisting of palmitic acid and stearic acid.

10. The satiety enhancing food, feed, beverage or food supplement according to claim 8, wherein said lipids are obtained from palm oil, palm stearine or shea butter, or fractionated palm oil, palm stearine or shea butter.

11. The satiety enhancing food, feed, beverage or food supplement according to claim 8, in the form of a dairy product, a dairy alternative product, ice cream, margarine, spread, dip, dressing or sauce, processed meat product, confectionary, filling, soup, fruit drink, tea or coffee-based drink, soft drink, near-water, beverages comprising maximum 35% dairy and/or lactic contents by volume, coffee creamer, dessert, chocolate, candy or other confectionary, baked good, nutrition bar, cereal bar, protein-based bar, pasta product and other cereal product, breakfast cereal, muesli, custard, or a meal replacement product.

12. A food, feed, beverage or food supplement which comprises a composition comprising a lipid and an emulsifier, wherein at least 45 w/w % of fatty acids of the lipid are C16 or higher saturated fatty acids, and wherein at least 20 w/w % of the lipid is in a crystal form, wherein said food, feed or beverage product has a calorie content in a range of 50-250 kcal per serving.

13. The food, feed, beverage or food supplement according to claim 12, wherein the lipids comprise at least one selected from the group consisting of palmitic acid and stearic acid.

14. The food, feed, beverage or food supplement according to claim 12, wherein said lipids are obtained from palm oil, palm stearine or shea butter, or fractionated palm oil, palm stearine or shea butter.

15. The food, feed, beverage or food supplement according to claim 12, in the form of a dairy product, a dairy alternative product, ice cream, margarine, spread, dip, dressing or sauce, processed meat product, confectionary, filling, soup, fruit drink, tea or coffee-based drink, soft drink, near-water, beverages comprising maximum 35% dairy and/or lactic contents by volume, coffee creamer, dessert, chocolate, candy or other confectionary, baked good, nutrition bar, cereal bar, protein-based bar, pasta product and other cereal product, breakfast cereal, muesli, custard, or a meal replacement product.

16. A method for preparing a satiety enhancing food, feed, beverage product or food supplement comprising adding to or incorporating into said food, feed or beverage a composition comprising a lipid and an emulsifier, wherein at least 45 w/w % of fatty acids of the lipid are C16 or higher saturated fatty acids, and wherein at least 20 w/w % of the lipid is in a crystal form.

17. A method for preparing a food, feed, beverage product or food supplement comprising adding to or incorporating into said food, feed or beverage a composition comprising a lipid and an emulsifier, wherein at least 45 w/w % of fatty acids of the lipid are C16 or higher saturated fatty acids, and wherein at least 20 w/w % of the lipid is in a crystal form, and wherein said food, feed or beverage product has a calorie content in the range of 50-250 kcal per serving.

18. The method according to claim 16 or 17, wherein said food is a dairy product, dairy alternatives, ice cream, margarine, spread, dip, dressing or sauce, processed meat product, confectionary, filling, soup, fruit drink, tea or coffee-based drink, soft drink, near-water, beverages comprising maximum 35% dairy and/or lactic contents by volume, coffee creamer, dessert, chocolate, candy or other confectionary, baked good, nutrition bar, cereal bar, protein-based bar, pasta product and other cereal product, breakfast cereal or muesli, custard, meal replacement product.

19. The method according to claim 16 or 17, wherein the lipids comprise at least one selected from the group consisting of palmitic acid and stearic acid.

20. The method according to claim 16 or 17, wherein said lipids are obtained from palm oil, palm stearine or shea butter, or fractionated palm oil, palm stearine or shea butter.

* * * * *